(12) United States Patent
Nagareda

(10) Patent No.: US 10,841,414 B2
(45) Date of Patent: Nov. 17, 2020

(54) INFORMATION TERMINAL, WRIST INFORMATION DEVICE, AND SYSTEM

(71) Applicant: CASIO COMPUTER CO., LTD., Tokyo (JP)

(72) Inventor: Hirofumi Nagareda, Tachikawa (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 16/589,180

(22) Filed: Oct. 1, 2019

(65) Prior Publication Data
US 2020/0106873 A1  Apr. 2, 2020

(30) Foreign Application Priority Data
Oct. 1, 2018 (JP) .................. 2018-186636

(51) Int. Cl.
| | |
|---|---|
| H04M 1/725 | (2006.01) |
| H04W 4/029 | (2018.01) |
| H04W 76/14 | (2018.01) |
| H04W 4/80 | (2018.01) |
| G04F 10/00 | (2006.01) |
| G04G 21/04 | (2013.01) |
| A61B 5/11 | (2006.01) |

(Continued)

(52) U.S. Cl.
CPC .......... *H04M 1/7253* (2013.01); *G04F 10/00* (2013.01); *G04G 9/007* (2013.01); *H04W 4/029* (2018.02); *H04W 4/80* (2018.02); *H04W 76/14* (2018.02)

(58) Field of Classification Search
CPC ..... H04M 1/7253; G04F 10/00; H04W 4/029; H04W 76/14; H04W 4/80; G04G 9/007
USPC ...................................... 455/456.1
See application file for complete search history.

(56) References Cited

U.S. PATENT DOCUMENTS 5,805,870 A * 9/1998 Browning .................. G06F 1/14
                                                    713/375
7,008,387 B2 * 3/2006 Saruwarati ............ A61B 5/1118
                                                    600/595

(Continued)

FOREIGN PATENT DOCUMENTS

| EP | 2 876 567 A1 | 5/2015 |
|---|---|---|
| JP | 2009-214591 A | 9/2009 |

(Continued)

OTHER PUBLICATIONS

Extended European Search Report dated Feb. 14, 2020 received in European Patent Application No. EP 19200502.3.

*Primary Examiner* — Inder P Mehra
(74) *Attorney, Agent, or Firm* — Scully Scott Murphy & Presser

(57) ABSTRACT

An information terminal is used with a wrist information device. The information terminal includes a position measurement module, communication circuit, a memory, and a processor. The position measurement module obtains position information. The communication circuit communicates with the wrist information device. The processor obtains information about an operation of a clock function input into the wrist information device during establishment of connection of the communication, obtains the position information from the position measurement module, and stores, in the memory, the position information and the information about the operation of the clock function in association with each other.

20 Claims, 11 Drawing Sheets

(51) Int. Cl.
*A61B 5/00* (2006.01)
*G04G 9/00* (2006.01)

(56) References Cited

U.S. PATENT DOCUMENTS

| | | | |
|---|---|---|---|
| 2010/0159881 A1* | 6/2010 | Yasaki | G06F 21/88 |
| | | | 455/411 |
| 2016/0004224 A1 | 1/2016 | Pi | |
| 2016/0163174 A1* | 6/2016 | Zhang | G08B 21/0438 |
| | | | 340/539.12 |
| 2017/0059326 A1* | 3/2017 | Zhang | H04B 1/3877 |
| 2017/0261331 A1* | 9/2017 | Shimizu | G01C 21/3469 |
| 2018/0157377 A1* | 6/2018 | Popov | G06F 3/048 |

FOREIGN PATENT DOCUMENTS

| | | | |
|---|---|---|---|
| JP | 2009-222407 A | 10/2009 | |
| JP | 2014-013204 A | 1/2014 | |
| JP | 2015-073809 A | 4/2015 | |
| JP | 6269237 B2 | 1/2018 | |

\* cited by examiner

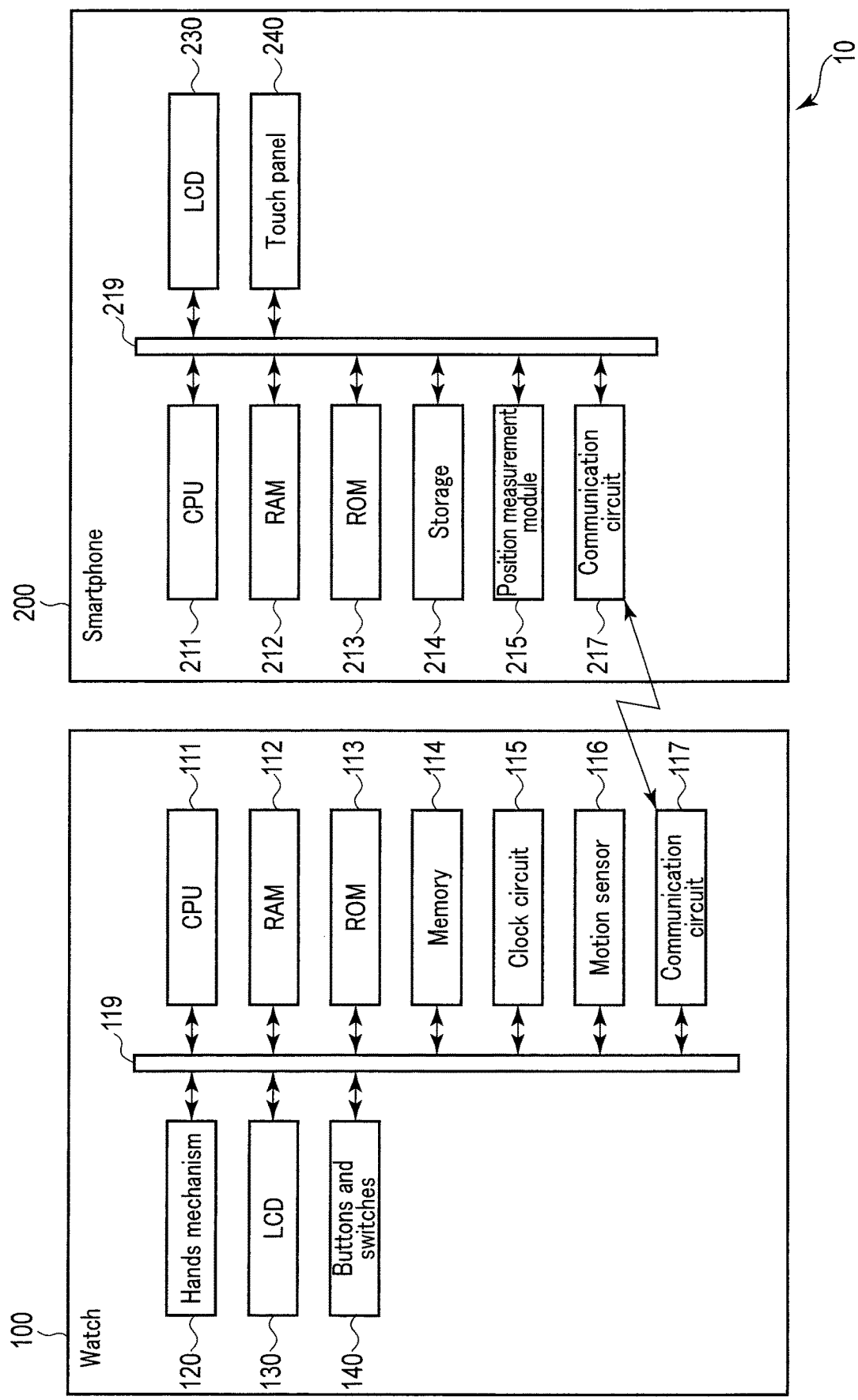
F I G 2

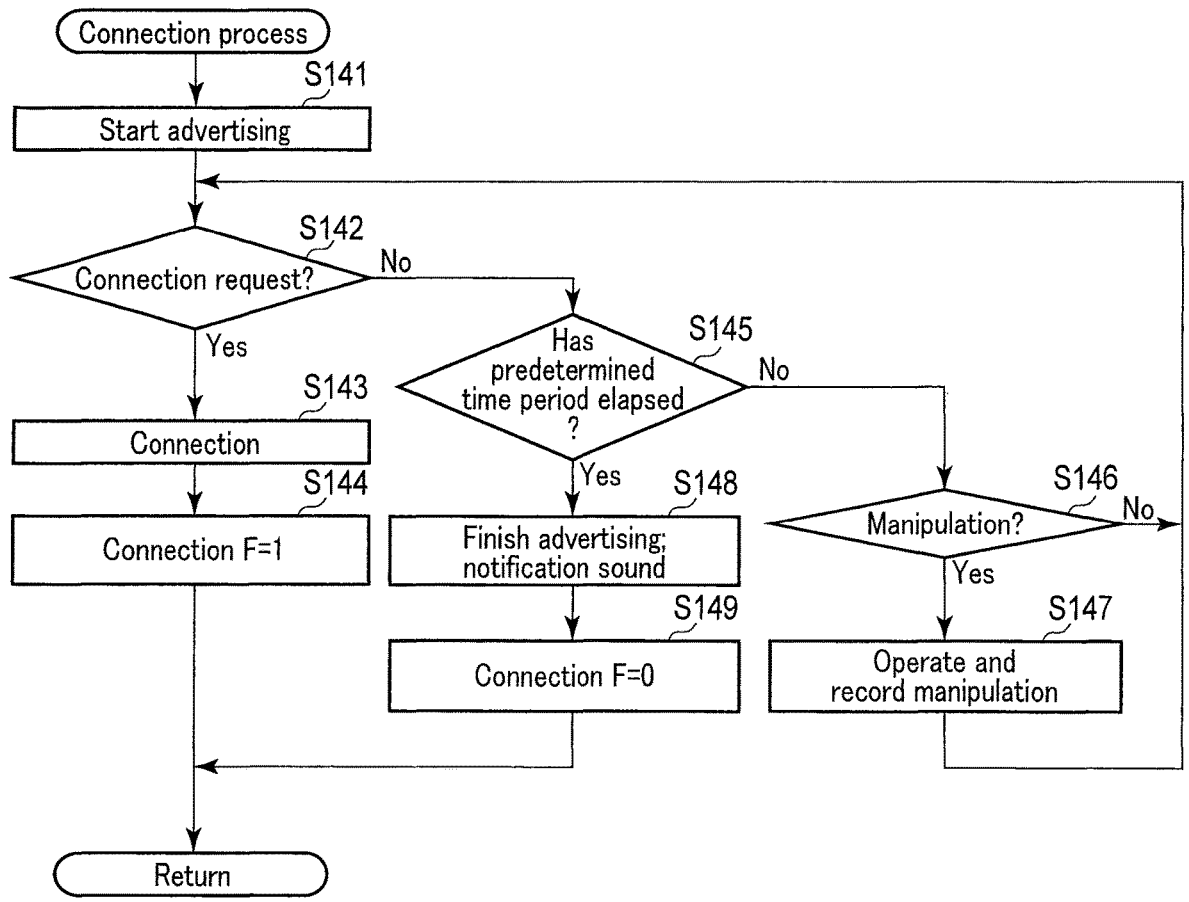
F I G. 3B

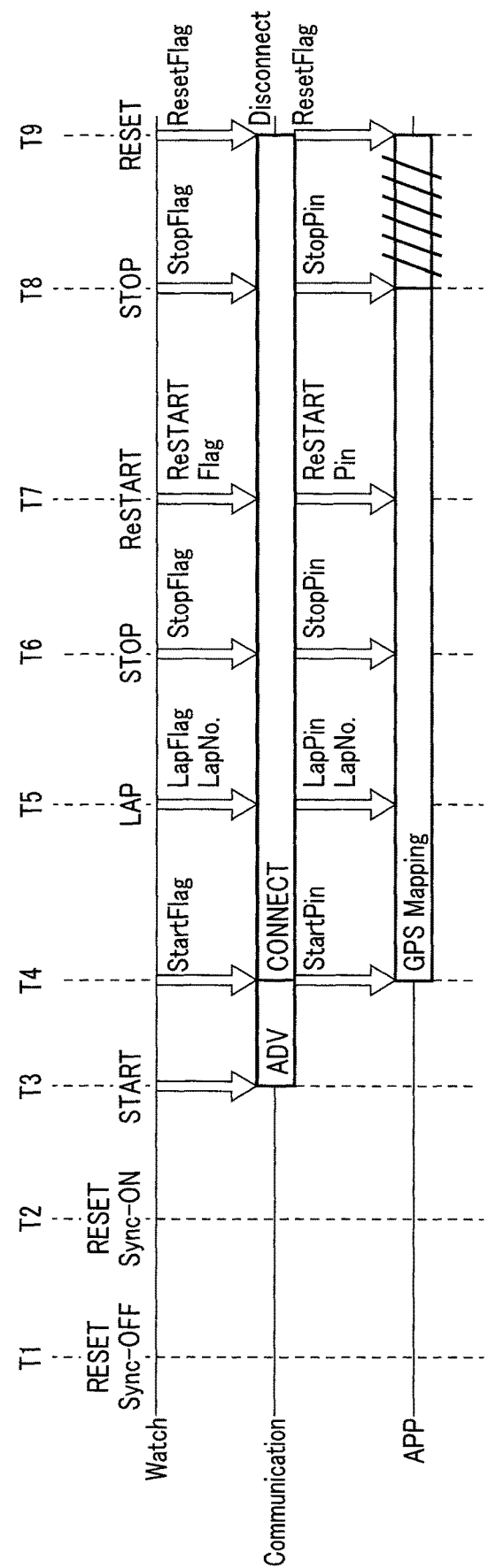
F I G. 5

FIG. 6

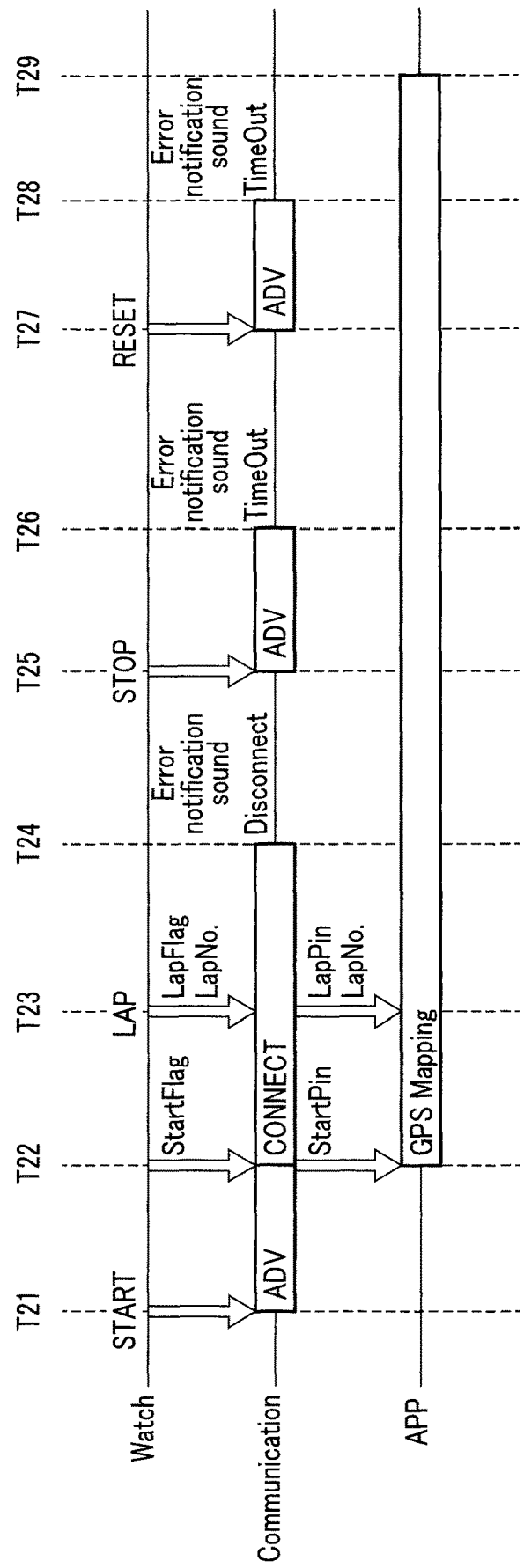
F I G. 8

INFORMATION TERMINAL, WRIST INFORMATION DEVICE, AND SYSTEM

CROSS-REFERENCE TO RELATED APPLICATIONS

This application is based upon and claims the benefit of priority from prior Japanese Patent Application No. 2018-186636, filed Oct. 1, 2018, the entire contents of which are incorporated herein by reference.

BACKGROUND

1. Technical Field

The technical field relates to an information terminal, a wrist information device, and a system.

2. Description of Related Art

For various purposes of managing the amount of exercise and improving the efficiency of training, the history of activities, such as walking, running, and cycling, are recorded. Among such history of activities, for example, the history of positions using a satellite positioning system is also valuable information.

For example, Jpn. Pat. Appln. KOKAI Publication No. 2009-222407 discloses a technique relating to a portable type walk support device that obtains the current position by the GPS (Global Positioning System) to measure a travel distance per unit time period, while measuring the number of steps per unit time period by an acceleration sensor. The portable type walk support device calculates the pace and pitch pertaining to a user's walk, presents them to the user, and provides the user with an advice pertaining to the pace and pitch.

A wrist information device, such as a watch, is fixed to a wrist of a user. Accordingly, the device has high operability. Meanwhile, since the wrist information device is fixed to a wrist of the user, the size is limited, and it is difficult to mount a large-capacity battery. Position detection using a satellite positioning system, such as the GPS, has a relatively large power consumption.

A mobile terminal, such as a smartphone, has a function of position detection and the like using a satellite positioning system, is mounted with a battery having a sufficient capacity, and is sometimes carried during walking, running, cycling and the like. On the other hand, the mobile terminal has a larger size than the wrist information device. Accordingly, the mobile terminal is unsuitable for operations during activities.

SUMMARY

In one embodiment, an information terminal, a wrist information device, and a system.

One embodiment includes the following configuration: an information terminal configured to be used with a wrist information device comprising an operation receiver and having a clock function, the information terminal comprising: a position measurement module configured to obtain position information using a satellite positioning system; a communication circuit configured to be capable of communication with the wrist information device; a memory; and a processor, wherein the processor is configured to: obtain information about an operation of the clock function input into the wrist information device, from the wrist information device via the communication circuit, during establishment of connection of the communication, obtain the position information obtained using the satellite positioning system, from the position measurement module, and store, in the memory, the position information and the information about the operation of the clock function in association with each other.

BRIEF DESCRIPTION OF THE DRAWINGS

FIG. 2 is a block diagram showing a configuration example of the system of the embodiment;

FIG. 3B is a flowchart showing an example of operations in the stopwatch mode of the watch of the embodiment;

FIG. 5 is a timing chart for illustrating an example of operations of the system of the embodiment;

FIG. 6 shows examples of screen transition of the watch of the embodiment;

FIG. 8 is a timing chart for illustrating an example of operations of the system of the embodiment;

DETAILED DESCRIPTION

An embodiment of the present invention is described with reference to the drawings. This embodiment relates to an information processing system that comprises a wrist information device having a stopwatch function (clock function), such as a watch, that measures an elapsed time, and an information terminal, such as a smartphone. The system of this embodiment can be used to record the history of activities, such as walking, running, and cycling, for various purposes of managing the amount of exercise and improving the efficiency of training. The watch and the smartphone can communicate with each other and operate in cooperation. It is a matter of course that the watch exerts functions as those of a typical timepiece that indicates the current time and the like. Furthermore, switching of operation modes allows the watch to exert functions as those of a stopwatch.

The stopwatch functions include a function of an asynchrony mode in which the watch solely functions, and a synchronization mode in which the watch functions in cooperation with the smartphone. In the synchronization mode, when a user uses the stopwatch function of the watch, information about an operation performed to the watch is transmitted to the smartphone. The smartphone uses the received information about the operation to perform operations in cooperation with the stopwatch function of the watch. In particular, the smartphone tracks the current position using a satellite positioning system, such as the GPS (Global Positioning System), for example, and adds an operation to the stopwatch input using the watch, and information about the elapsed time measured using the stopwatch function, to the current position information.

[System Configuration]

Figure 1:
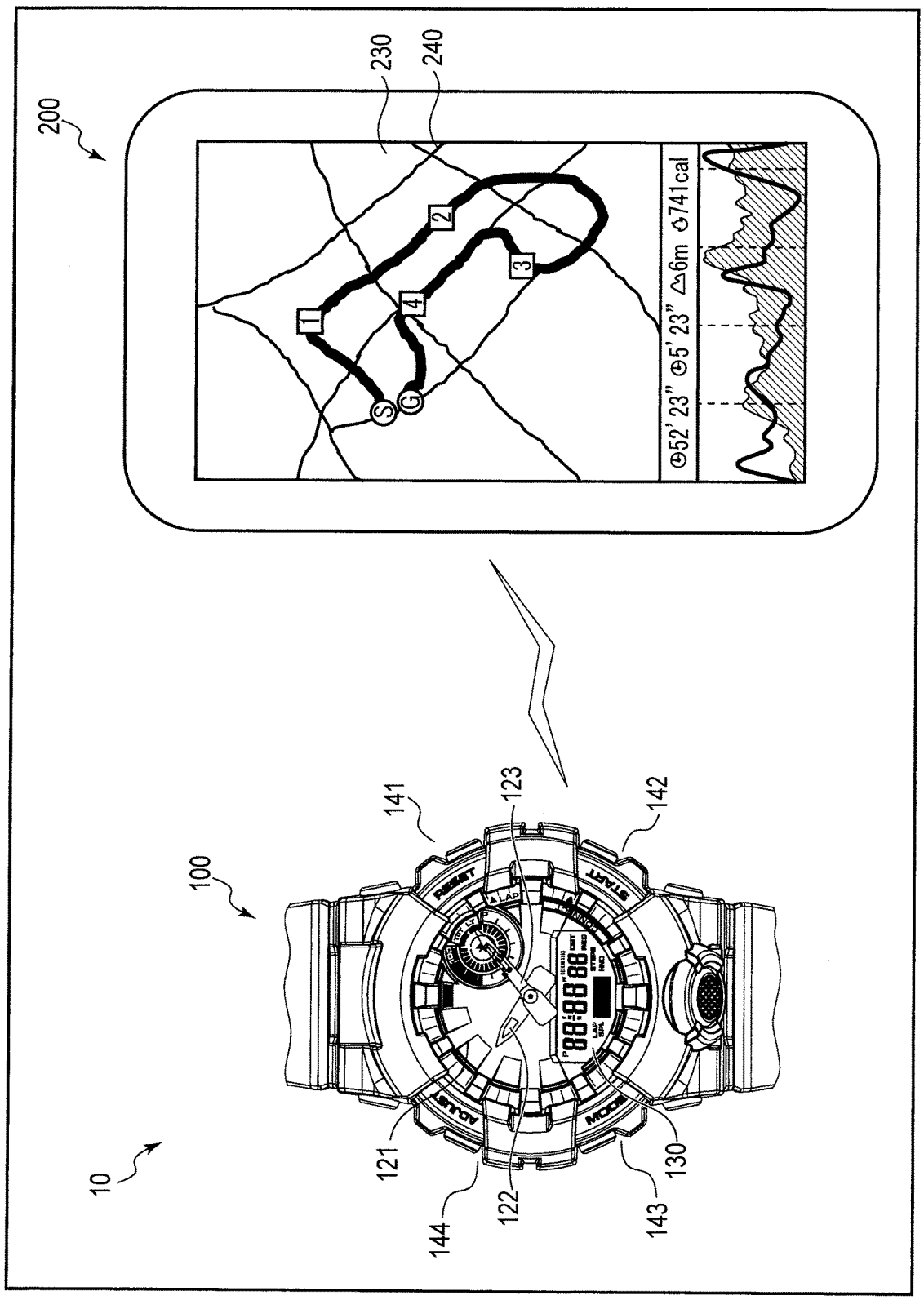
FIG. 1 shows an example of an appearance of a system of an embodiment.

FIG. 1 shows an overview of the appearance of the system 10 of this embodiment. The system 10 comprises a watch 100, and a smartphone 200. The watch 100 has the stopwatch function. In the example shown in FIG. 1, the watch 100 comprises a watch face 121, an hour hand 122, and a minute hand 123 and the like that are for indicating the time. The watch 100 comprises a liquid crystal display (LCD) 130. The LCD 130 displays a result of measurement by the stopwatch, for example. The watch 100 comprises buttons as an operation receiver for allowing operations pertaining to various functions of the watch 100, such as of the stopwatch. The buttons comprise a reset button 141, a start button 142, a mode button 143 and an adjust button 144. The smartphone 200 comprises an LCD 230 as a display device, and a touch panel 240 as an input device. The watch 100 and the smartphone 200 are connected to each other through wireless communication. For this wireless communication, an energy-saving near field wireless communication technique, such as Bluetooth Low Energy (Bluetooth is a trademark), for example, can be used. Use of an energy-saving communication technique can reduce the power consumption of the system 10.

FIG. 2 is a block diagram showing an overview of a configuration example of the system 10. The watch 100 comprises a CPU (Central Processing Unit) 111, a RAM (Random Access Memory) 112, a ROM (Read Only Memory) 113, a memory 114, a clock circuit 115, a motion sensor 116, a communication circuit 117, a hands mechanism 120, an LCD 130, and buttons and switches 140, which are connected to each other via a bus line 119.

The CPU 111 performs various types of signal processing and the like. The RAM 112 functions as a main memory device for the CPU 111. The ROM 113 stores various programs. The memory 114 comprises, for example, a semiconductor memory. The memory 114 can record information on the elapsed time measured by the stopwatch function of the watch 100. Besides the CPU 111 or instead of the CPU 111, one or more integrated circuits, such as an ASIC (Application Specific Integrated Circuit) and an FPGA (Field Programmable Gate Array), may be used.

The clock circuit 115 measures the time and the like, and achieves functions of clock, stopwatch and the like. The motion sensor 116 comprises, for example, an acceleration meter, an angular velocity meter, a magnetic sensor for obtaining the bearing, and a barometer for obtaining the altitude. For example, the number of steps can be measured based on a value detected by the motion sensor 116. The communication circuit 117 is used for communication with the smartphone 200 and the like.

The hands mechanism 120 comprises a drive mechanism for driving the hour hand 122, the minute hand 123 and the like. The LCD 130 is a display device that displays an elapsed time measured using the stopwatch function described above. The buttons and switches 140 comprise switches, such as the aforementioned reset button 141, start button 142, mode button 143 and adjust button 144.

The smartphone 200 comprises a CPU 211, a RAM 212, a ROM 213, a storage 214, a position measurement module 215, a communication circuit 217, the LCD 230, and the touch panel 240, which are connected to each other via a bus line 219. The CPU 211 serves as a control circuit, and performs various types of signal processing and various operations, for example, controls each element of the smartphone 200. The RAM 212 functions as a main memory device for the CPU 211. The ROM 213 stores an activation program and the like. As the storage 214, for example, an eMMC (Embedded Multi Media Card), an SSD (Solid State Drive) and the like are adopted. The storage 214 stores various types of information, such as programs and parameters, to be used by the CPU. The storage 214 serves as a storage device, and stores information obtained from the watch 100, information obtained by the smartphone 200, information that associates these pieces of information with each other, and the like. Besides the CPU 211, various integrated circuits, such as an ASIC, an FPGA and a GPU (Graphics Processing Unit), may be used as the control circuit. Any number of integrated circuits may be used. Instead of the LCD 230, another device, such as an organic EL display, may be adopted as the display device.

The position measurement module 215 detects the position using a satellite positioning system. The position measurement module 215 receives, for example, radio waves transmitted from a navigation satellite, such as a GPS satellite, using an antenna. The position measurement module 215 generates information about the current position, based on information about the radio waves. The position measurement module 215 is not limited to the GPS, but may be what uses any of various GNSSs (Global Navigation Satellite Systems) including a quasi-zenith satellite system. The communication circuit 217 communicates with the communication circuit 117 of the watch 100 and the like. The communication circuit 217 may comprise what communicates with the watch 100, such as a Bluetooth module. The communication circuit 217 can comprise a communication module for connection to a wireless LAN, a mobile phone line and the like. The LCD 230 functions as a display device as described above. The touch panel 240 functions as an input device as described above.

[Overview of System Operation]

In this embodiment, a start operation, a stop operation, a restart operation, a lap operation, a reset operation and the like of the stopwatch are performed using the start button 142, the reset button 141 and the like of the watch 100. Here, the start operation is an operation for starting measurement of the elapsed time. The start operation is performed by, for example, pressing the start button 142 in a state where measurement has been reset. The stop operation is an operation for stopping the measurement of the elapsed time. The stop operation is performed by, for example, pressing the start button 142 during measurement of the elapsed time. The restart operation is an operation that starts again after a stop of measurement by the stop operation and continues the measurement. The restart operation is performed by, for example, pressing the start button 142 in a state where the measurement has been stopped by the stop operation. The lap operation is an operation for measuring a lap time. The lap operation is performed by, for example, pressing the reset button 141 during measurement of the elapsed time. The reset operation is an operation of resetting the measurement of the elapsed time. The reset operation is performed by, for example, pressing the reset button 141 in a state where the measurement has been stopped by the stop operation.

The watch 100 displays, on the LCD 130, a measurement result of an elapsed time and the like according to an operation by the user. The watch 100 records a history of operations by the user, elapsed times measured when the operations by the user are performed, and times when the operations by the user are performed as required. When any of various operations pertaining to the stopwatch function is performed to the watch 100, the watch 100 transmits the content of the operation to the smartphone 200 through wireless communication. The watch 100 may transmit, to the smartphone 200, other various types of information, for example, accumulated information that includes the relationship between the history of operations by the user, the times when the operations by the user are performed, and elapsed times measured when the operations by the user are performed.

The smartphone 200 has a position measurement function using the satellite positioning system. Upon receipt of a signal pertaining to the start operation from the watch 100, the smartphone 200 starts position measurement, and records information about the start operation in association with information on the current position. The smartphone 200 periodically records the current position after starting the position measurement. Upon receipt of signals pertaining to the lap operation, the stop operation or the like from the watch 100, the smartphone 200 records information about the operation in association with the information on the current position. Upon receipt of a signal pertaining to the reset operation from the watch 100, the smartphone 200 finishes the position measurement, and removes unnecessary information. The smartphone 200 may receive other various types of information from the watch 100, and record the information.

The smartphone 200 may display, based on the various types of information that include the recorded position information, the operation information for the watch 100, and the accumulated information received from the watch 100. The displays may include a history of variation in position information accompanied by the lapse of time, information on positions where the start operation, the lap operation and the stop operation are performed, a calorie (calorie consumption) that has been consumed by a series of activities and obtained by analysis based on the time period from start to stop, each lap time, variation in height difference, and recorded information, and information on the velocity and the pace indicated by the required time period per unit distance.

Figure 3A:
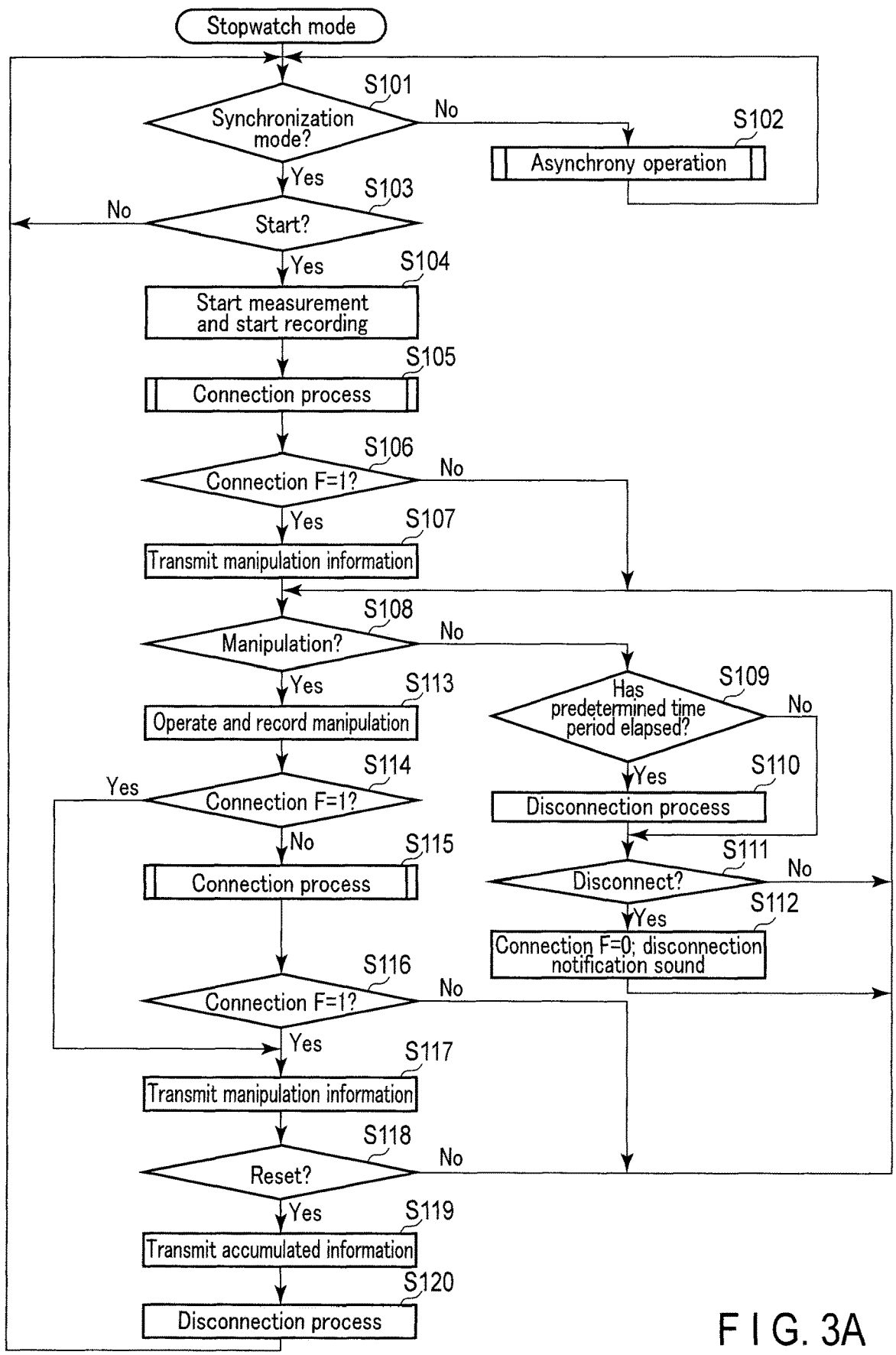
FIG. 3A is a flowchart showing an example of operations in a stopwatch mode of a watch of the embodiment.

The aforementioned operations pertaining to the stopwatch function that the watch 100 has are described with reference to flowcharts shown in FIGS. 3A and 3B. The operations described here are operations performed when the stopwatch mode is selected using the mode button 143.

In Step S101, the watch 100 determines whether or not the mode is the synchronization mode for performing the operations of the stopwatch in cooperation with the smartphone 200. If the mode is not the synchronization mode, the processing proceeds to Step S102. In Step S102, the watch 100 does not cooperate with the smartphone 200, but solely exerts the stopwatch function. For example, the watch 100 starts to measure the elapsed time when the start button 142 is pressed, and stops the measurement when the start button 142 is pressed next time. The watch 100 measures a lap time when the reset button 141 is pressed during measurement of the elapsed time. The watch 100 displays the elapsed time during measurement, on the LCD 130.

If it is determined that the mode is the synchronization mode in Step S101, the processing proceeds to Step S103. In Step S103, the watch 100 determines whether the start button 142 has been pressed or not, that is, whether a command of starting to measure the elapsed time has been input or not. If the start button 142 has not been pressed, the processing returns to Step S101. The watch 100 stands by for pressing of the start button 142. When the start button 142 is pressed, the processing proceeds to Step S104.

In Step S104, the watch 100 starts to measure the elapsed time. Furthermore, the watch 100 starts to record information pertaining to the stopwatch. For example, the time when the measurement is started is recorded.

Besides starting of the measurement, in Step S105, the watch 100 starts a connection process in order to establish communication with the smartphone 200 through Bluetooth Low Energy, for example. The connection process is described with reference to FIG. 3B.

In Step S141, the watch 100 starts advertising. The watch 100 starts to transmit an advertising packet. At this time, the smartphone 200 having received the advertising packet transmitted from the watch 100 is expected to issue a connection request to the watch 100.

In Step S142, the watch 100 determines whether the connection request is issued from the smartphone 200 or not. If the connection request is issued from the smartphone 200, the processing proceeds to Step S143. In Step S143, the watch 100 establishes connection with the smartphone 200 according to predetermined procedures. Subsequently, the processing proceeds to Step S144. In Step S144, the watch 100 sets a connection flag (connection F) to one, and finishes the connection process.

In Step S142, if it is determined that the connection request has not been issued by the smartphone 200, the processing proceeds to Step S145. In Step S145, the watch 100 determines whether a predetermined time period has elapsed or not. The time period is, for example, 10 seconds. The predetermined time period is not limited thereto. If it is determined that the predetermined time period has not elapsed yet, the processing proceeds to Step S146.

In Step S146, the watch 100 determines whether an operation has been performed or not. If no operation has been performed, the processing returns to Step S142. That is, the advertising is continued, and the process for connecting communication with the smartphone 200 is continued.

In Step S146, if it is determined that the operation has been performed, the processing proceeds to Step S147. In Step S147, the watch 100 operates according to the performed operation, and records the operation. For example, if the start button 142 is pressed during measurement, the measurement is temporarily stopped, and a measurement value at the time and this time are recorded. For example, when the reset button 141 is pressed, the lap time is displayed, and the lap time, the time and the like are recorded. Subsequently, the processing returns to Step S142. The process for connecting communication with the smartphone 200 is continued.

In Step S145, if it is determined that the predetermined time period has elapsed, the processing proceeds to Step S148. In Step S148, the watch 100 finishes transmission of advertising signals. That is, the watch 100 stops the process for connecting communication with the smartphone 200. To notify the user of a failure in connection with the smartphone 200, a sound representing the fact is output. Subsequently, the processing proceeds to Step S149. In Step S149, the watch 100 sets the connection flag to zero, and finishes the connection process.

As described above, until the predetermined time period elapses, the watch 100 continues the trial of connecting with the smartphone 200, and when an operation is performed during the trial, the watch 100 performs and records the operation according to the operation. If the predetermined time period has elapsed (timeout), the process for connecting communication is stopped, and this fact is notified to the user.

Returning to FIG. 3A, the description is continued. In Step S106, the watch 100 determines whether the connection flag is one or not. If the connection flag is zero, the processing proceeds to Step S108. If the connection flag is one, the processing proceeds to Step S107. In Step S107, the watch 100 transmits, to the smartphone 200, information about the operations recorded by then. Subsequently, the processing proceeds to Step S108. The smartphone 200 having received the information about the operation performs the operation according to the operation.

In Step S108, the watch 100 determines whether an operation has been performed or not. If it is determined that no operation is performed, the processing proceeds to Step S109. In Step S109, the watch 100 determines whether the predetermined time period has elapsed or not. The predetermined time period can be set by the user. The time period is, for example, 30 minutes, one hour or the like. The predetermined time period is not limited thereto. Setting corresponding to causing the predetermined time period to be infinity, that is, setting of turning off the timeout function may be performed. If it is determined that the predetermined time period has not elapsed yet, the processing proceeds to Step S111.

In Step S109, if it is determined that the predetermined time period has elapsed, the processing proceeds to Step S110. In Step S110, the watch 100 issues a request for disconnection to the smartphone 200. In response to the request, a disconnection process is performed. Subsequently, the processing proceeds to Step S111.

As described above, if no operation has been performed for a predetermined time period, it is believed that the measurement is continuing even though the user does not wish to measure the elapsed time. In such a case, disconnection of communication can suppress needless power consumption. In Step S110, the connection is intentionally disconnected because no operation is performed for the predetermined time period. However, the connection is sometimes unintentionally disconnected owing to various factors, such as unreachable radio waves.

In Step S111, the watch 100 determines whether the connection with the smartphone 200 has been disconnected intentionally or unintentionally. In cases where no disconnection is detected, including a case where a state of continuing disconnection, the processing returns to Step S108. That is, the watch 100 stands by for an operation to be performed by the user.

In Step S111, when disconnection is detected, the processing proceeds to Step S112. In Step S112, the watch 100 sets the connection flag to zero. To notify the user of disconnection, the watch 100 outputs a sound representing the disconnection. Subsequently, the processing returns to Step S108, and stands by for an operation by the user.

In Step S108, if it is determined that an operation has been performed by the user, the processing proceeds to Step S113. In Step S113, the watch 100 operates according to the performed operation, and records the operation. Subsequently, the processing proceeds to Step S114.

In Step S114, the watch 100 determines whether the connection flag is one or not, that is, whether to be in connection with the smartphone 200 or not. If the state is in connection, the processing proceeds to Step S117. If the state is not in connection, the processing proceeds to Step S115. In Step S115, the watch 100 performs the connection process. The connection process is as described above with reference to FIG. 3B. Subsequently, in Step S116, the watch 100 determines whether the connection flag is one or not, that is, whether to be in connection with the smartphone 200 or not. If the state is not in connection, the processing returns to Step S108. That is, an operation by the user is waited for again. If the state is in connection, the processing proceeds to Step S117.

In Step S117, the watch 100 transmits, to the smartphone 200, the operation information having been recorded but have not been transmitted yet. When an operation is performed by the user, the watch 100 transmits the operation information to the smartphone 200 immediately if being connected to the smartphone 200. If not being connected to the smartphone 200, the watch 100 establishes connection thereto and subsequently transmits the operation information to the smartphone 200.

In Step S118, the watch 100 determines whether the operation performed by the user is a reset operation or not. If the operation is not the reset operation, the processing returns to Step S108. That is, the watch 100 stands by for a next operation to be performed by the user. If the operation is the reset operation, the processing proceeds to Step S119.

In Step S119, the watch 100 transmits, to the smartphone 200, the information having been accumulated in the memory 114. The information can include series of pieces of information about a history of the start operation, the lap operation, the stop operation, the restart operation, the reset operation and the like, elapsed times measured according to these operations, and times at which these operation were performed. Subsequently, in Step S120, the watch 100 issues a request for disconnecting communication to the smartphone 200, and disconnects the connection according to predetermined procedures. Subsequently, the processing returns to Step S101. That is, as described above, the watch 100 stands by for pressing again of the start button 142.

Figure 4:
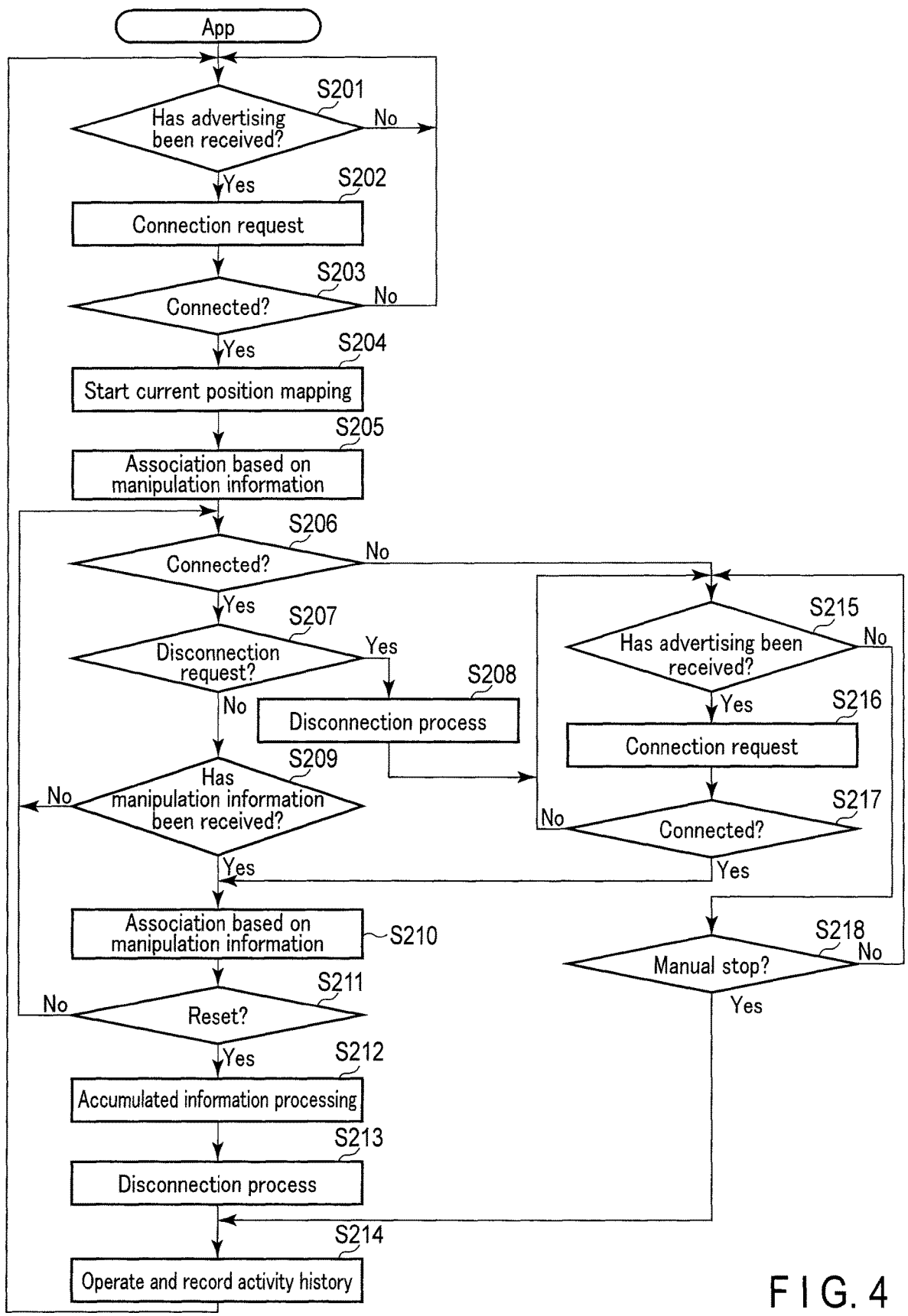
FIG. 4 is a flowchart showing an example of operations in a stopwatch mode of a smartphone of the embodiment.

Operations of the smartphone 200 pertaining to the stopwatch function in the synchronization mode are described with reference to a flowchart shown in FIG. 4. The operations described here are operations when application software (application) operating in the smartphone 200 in cooperation with the watch 100 is in activation, and the operations pertaining to the stopwatch function are now described.

In Step S201, the smartphone 200 determines whether or not the watch 100 has received the advertising packet transmitted by the watch 100. If the advertising packet has not been received, the processing repeats Step S201. That is, the smartphone 200 stands by for receipt from the watch 100. When the smartphone 200 receives the advertising packet, the processing proceeds to Step S202.

In Step S202, the smartphone 200 transmits a connection request to the watch 100, based on the information included in the advertising packet. Based on this connection request, predetermined procedures are performed between the watch 100 and the smartphone 200 and connection therebetween is expected to be established.

In Step S203, the smartphone 200 determines whether the connection is established or not. If the connection is not established, the processing returns to Step S201. That is, the process described above is repeated until the connection is established with the watch 100. If the connection is established, the processing proceeds to Step S204.

In Step S204, the smartphone 200 obtains the current position of the smartphone 200 using the satellite positioning system. Hereinafter, the smartphone 200 periodically obtains the current position, and tracks the travel of the smartphone 200. That is, a list of pieces of position information at the respective times is created. The position information is associated with map information, and can present the trajectory of travel.

In Step S205, the smartphone 200 records the operation information obtained from the watch 100 in association with the position information described above. For example, the positions at which operations, such as the start operation, the lap operation, and the stop operation, have been performed to the watch 100 are recorded in association therewith. Based on these pieces of information, the trajectory of travel of the user carrying the watch 100 and the smartphone 200 can be drawn on a map, and furthermore, the positions at which the operations, such as the start operation, the lap operation, and the stop operation, have been performed can be indicated. Such a process of associating the position information obtained by the smartphone 200 with the operation information obtained by the watch 100 is called "association."

In Step S206, the smartphone 200 determines whether connection with the watch 100 is maintained or not. If the connection is maintained, the processing proceeds to Step S207. In Step S207, the smartphone 200 determines whether a disconnection request has been issued by the watch 100 or not. For example, according the operations of the watch 100 described above, in Step S110 and Step S120, the disconnection request is transmitted to the smartphone 200.

If the disconnection request has been transmitted, the processing proceeds to Step S208. In Step S208, the smartphone 200 performs the disconnection process. That is, the smartphone 200 issues a request for the disconnection to the watch 100 according to predetermined procedures, and thus disconnects the connection. Subsequently, the processing proceeds to Step S215.

In Step S207, if it is determined that no disconnection request has been issued, the processing proceeds to Step S209. In Step S209, the smartphone 200 determines whether it has received operation information from the watch 100 or not. If the smartphone 200 determines that no operation information has been received from the watch 100, the processing returns to Step S206. That is, while the connection is maintained, the smartphone 200 stands by for receipt of the operation information from the watch 100.

If the smartphone 200 determines that the operation information has received from the watch 100 in Step S209, the processing proceeds to Step S210. In Step S210, the smartphone 200 performs the association of associating the operation information obtained from the watch 100 with the position information obtained by the smartphone 200.

In Step S211, the smartphone 200 determines whether or not the operation information obtained from the watch 100 is information about resetting. If the information is not about resetting, the processing returns to Step S206. That is, the smartphone 200 repeats the reception and association of the operation information from the watch 100.

In Step S211, if it is determined that the operation information is the information about resetting, the processing proceeds to Step S212. In Step S212, the smartphone 200 performs accumulated information processing. That is, if the operation information is about the information about resetting, the watch 100 transmits the accumulated information to the smartphone 200 in the process of Step S119. The smartphone 200 receives the accumulated information, and records various types of information from start to stop in association with the information obtained by the smartphone 200.

At this time, the watch 100 transmits the disconnection request to the smartphone 200 in the process of Step S120. In Step S213, the smartphone 200 receives the disconnection request, performs predetermined disconnection procedures, and disconnects the connection between the watch 100 and the smartphone 200. The smartphone 200 finishes obtaining the current position using the satellite positioning system.

In Step S214, based on a series of the pieces of information, the smartphone 200 organizes the information from start to resetting as a history of activities, performs various operations to calculate information to be added, and records the information. The information to be added is, for example, an average pace, which is an average required time period per predetermined distance pertaining to travel, or a calorie consumed in a series of activities. Subsequently, the processing returns to Step S201.

If it is determined that the state is not in connection in Step S206, the processing proceeds to Step S215. In Step S215, the smartphone 200 determines whether the advertising packet transmitted from the watch 100 has been received or not. Even in case the connection is disconnected by any reason, when an operation is input into the watch 100, the watch 100 performs advertising in order to establish connection with the smartphone 200 as in the process of Step S115 by the watch 100. In such a case, the smartphone 200 receives the advertising packet transmitted from the watch 100.

When the smartphone 200 receives the advertising packet, the processing proceeds to Step S216. In Step S216, the smartphone 200 transmits a connection request to the watch 100, and tries to establish connection according to the predetermined procedures.

In Step S217, the smartphone 200 determines whether the connection with the watch 100 is established or not. If the connection is established, the processing proceeds to Step S210. That is, the smartphone 200 receives, from the watch 100, the operation information serving as a trigger of the connection process, and performs association based on the operation information. When the connection is not established, the processing returns to Step S215, and the smartphone 200 stands by for receipt of the advertising packet output from the watch 100.

If it is determined that the advertising packet has not been received in Step S215, the processing proceeds to Step S218. In Step S218, the smartphone 200 determines whether or not the user's command for stopping obtaining the position information has been input into the touch panel 240 of the smartphone 200. When a manual stop command is not input, the processing returns to Step S215, and the smartphone 200 stands by for receipt of the advertising packet output from the watch 100. On the other hand, when the manual stop command is input, the processing proceeds to Step S214. That is, the smartphone 200 organizes the information until manual stop, as a history of activities, operates additional information, and records the information.

Figure 6:
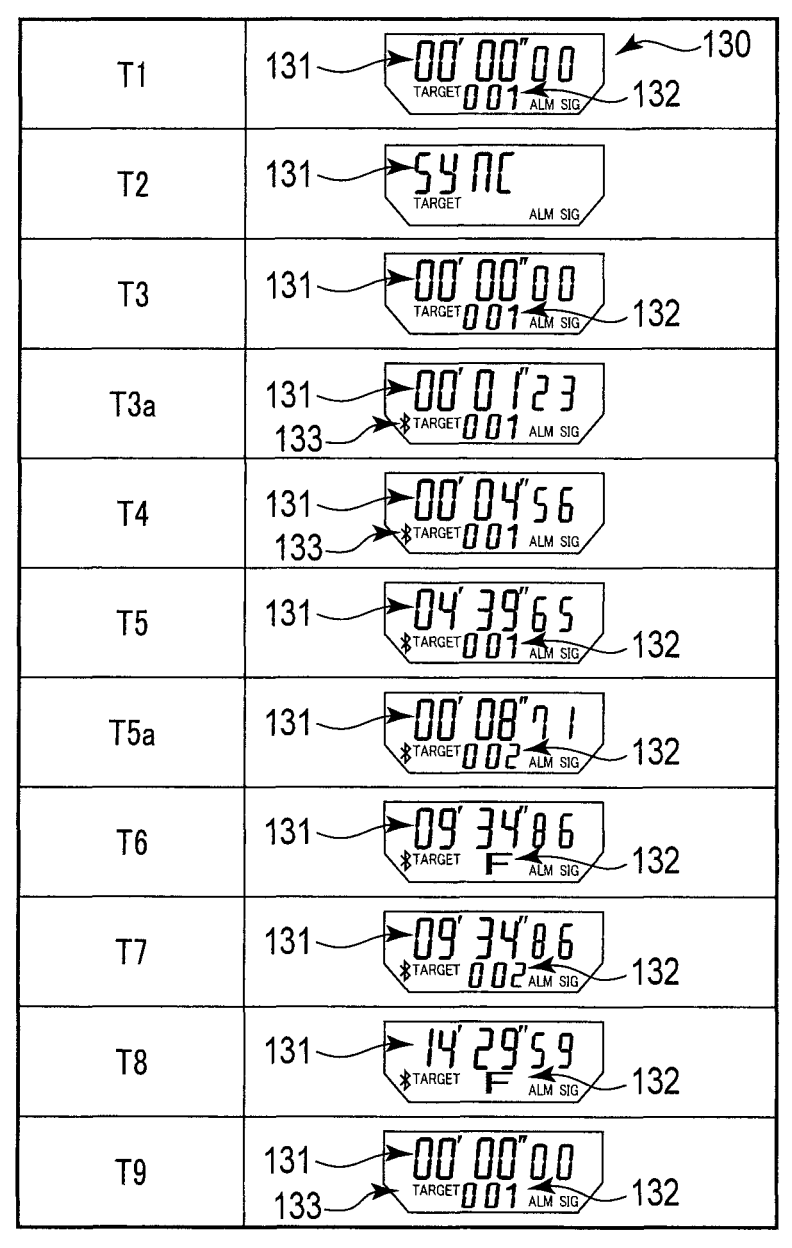

An example of operations of the system 10 in this embodiment is described. FIG. 5 is a timing chart showing an operation example of the watch 100 and the smartphone 200. An upper part schematically shows input into the watch 100, and information transmitted to the smartphone 200 at each timing. A middle part schematically shows a connection state between the watch 100 and the smartphone 200. A lower part schematically shows the operation state of the application of the smartphone 200. FIG. 6 shows examples of screens to be displayed on the LCD 130 at each timing shown in FIG. 5.

As shown in FIG. 5, it is assumed that at time T1, the synchronization mode is off. The stopwatch is in a reset state. As shown in FIG. 6, in the state at time T1, "00'00"00" is displayed in a display area 131 for the measurement time to be displayed on the LCD 130. Since it is before start, "001" is displayed in a display area 132 for the number of laps.

It is assumed that as shown in FIG. 5, at time T2, the mode button 143 is operated, and the synchronization mode is changed to on. At this time, as shown in FIG. 6, "Sync" is displayed in the display area 131 for the measurement time in the LCD 130 for a predetermined time period, for example, several seconds. The mode is changed to the synchronization mode. However, at this time, the watch 100 and the smartphone 200 are not connected to each other, and the operation for connection is not performed either.

It is assumed that as shown in FIG. 5, at time T3, the start button 142 is pressed. At this time, the process of Step S104 in the watch 100 starts measurement, and starts recording. At the instant of starting, the measurement time is zero second. Accordingly, as shown in FIG. 6, "00'00"00" is displayed in the display area 131 for the measurement time. Since it is the first lap, "001" is displayed in the display area 132 for the number of laps. At this time, in Step S105 by the watch 100, the connection process is performed. In Step S141, advertising is started. As shown in FIG. 5, the advertising is performed from time T3 at which the start button 142 is pressed to a time at which the advertising is found by the smartphone 200 to establish connection. By establishment of connection, it takes four to five seconds, for example.

T3a in FIG. 6 indicates display from start to establishment of connection. In the display area 131 for the measurement time, the measurement time is displayed. In a Bluetooth display area 133 therebelow, a mark of "Bluetooth" is lighted up.

It is assumed that as shown in FIG. 5, at time T4, connection is established. At this time, as shown in FIG. 6, at time T4, display of "Bluetooth" in the Bluetooth display area 133 is lighted up. By the process of Step S107 by the watch 100, operation information that the start button 142 is pressed (StartFlag) is transmitted from the watch 100 to the smartphone 200 through the communication. In the process of Step S204, the smartphone 200 having received the signal starts position measurement using the satellite positioning system, such as the GPS, and starts mapping. In Step S205, the smartphone 200 performs association of start. That is, the measured position is recorded as a position at which the start operation has been performed. A time period of several seconds is required by establishment of connection by the connection process started by the start operation. Accordingly, the position at which the smartphone 200 has received the information about the start operation is different from the position at which the start operation has been input into the watch 100. However, the difference is very small and can be ignored. Accordingly, in this embodiment, the current position measured when communication is established is recorded as the position at which the start operation is performed.

It is assumed that as shown in FIG. 5, at time T5, the reset button 141 is pressed, and a lap measurement input is performed. At this time, as shown in T5 in FIG. 6, the watch 100 displays the lap time in the display area 131 for the measurement time, according to the process of Step S113. Since the number of laps is one, "001" is displayed in the display area 132 for the number of laps. This display is maintained for a several seconds. Subsequently, as shown in T5a in FIG. 6, the number of laps is two, "002" is displayed in the display area 132 for the number of laps, and the lap time of the second lap is displayed in the display area 131 for the measurement time.

According to the process of Step S117, the watch 100 transmits information that the lap operation has been performed (LapFlag), and information that the lap is the first lap (LapNo.) to the smartphone 200. The smartphone 200 having received the information associates the number of laps to thus perform association pertaining to the lap according to the process of Step S210. That is, the position at which the lap operation is performed is recorded.

It is assumed that as shown in FIG. 5, at time T6, the start button 142 is pressed, and a stop input is performed. At this time, as shown in T6 in FIG. 6, the watch 100 displays the lap time in the display area 131 for the measurement time, according to the process of Step S113. Since a stop command is issued, "F" is displayed in the display area 132 for the number of laps. This display is maintained until the next operation is performed.

According to the process of Step S117, the watch 100 transmits, to the smartphone 200, information that the stop command has been input (StopFlag). The smartphone 200 having received the information performs association pertaining to the stop according to the process of Step S210. That is, the position at which the stop operation is performed is recorded.

It is assumed that as shown in FIG. 5, at time T7, the start button 142 is pressed, and a restart input is performed. At this time, as shown in T7 in FIG. 6, the watch 100 restarts to measure the elapsed time according to the process of Step S113. The watch 100 displays the elapsed time after restart of measurement, in the display area 131 for the measurement time. Since the number of laps is still two in this case, "002" is displayed in the display area 132 for the number of laps.

According to the process of Step S117, the watch 100 transmits information that the restart command has been input (ReSTARTFlag) to the smartphone 200. The smartphone 200 having received the information performs association pertaining to the restart according to the process of Step S210.

It is assumed that as shown in FIG. 5, at time T8, the start button 142 is pressed, and a stop input is performed. At this time, as shown in T8 in FIG. 6, the watch 100 displays the lap time in the display area 131 for the measurement time, according to the process of Step S113. Since a stop command is issued, "F" is displayed in the display area 132 for the number of laps. This display is maintained until the next operation is performed.

According to the process of Step S117, the watch 100 transmits, to the smartphone 200, information that the stop command has been input (StopFlag). The smartphone 200 having received the information performs association pertaining to the stop according to the process of Step S210.

It is assumed that as shown in FIG. 5, at time T9, the reset button 141 is pressed, and a reset input is performed. At this time, as shown in T9 in FIG. 6, the watch 100 resets the display in the display area 131 for the measurement time to "00'00"00" according to the process of Step S113. "001" is displayed in the display area 132 for the number of laps. This display is maintained until the next operation is performed.

According to the process of Step S117, the watch 100 transmits information that the reset command has been input (ResetFlag) to the smartphone 200. The watch 100 transmits the accumulated information required in Step S119, to the smartphone 200. In Step S120, the watch 100 transmits the disconnection request to the smartphone 200. The smartphone 200 having received the information records the information about resetting according to the process of Step S210. The smartphone 200 processes information about the accumulated information according to the process of Step S212. The smartphone 200 disconnects the connection to the watch 100 according to the process of Step S213. Resultantly, as shown in FIG. 5, the connection is disconnected. The smartphone 200 finishes obtaining the current position information according to the process of Step S214, and removes the position information in the stop operation at time T8 and thereafter as unnecessary information. By removing the position information in the stop operation at time T8 and thereafter, only the position information during measurement of the elapsed time is stored. Accordingly, the information does not include information unnecessary for the user, and can be easily recognized.

As described above, when the start operation is performed to the watch 100, the watch 100 and the smartphone 200 are connected to each other. When the reset operation is performed to the watch 100, the connection is disconnected. Consequently, in particular, the watch 100 can reduce the consumption of the battery due to communication. The information on the operations performed to the watch 100 is shared with the smartphone 200. Accordingly, information processing according to the command input into the watch 100 can be performed.

Figure 7:
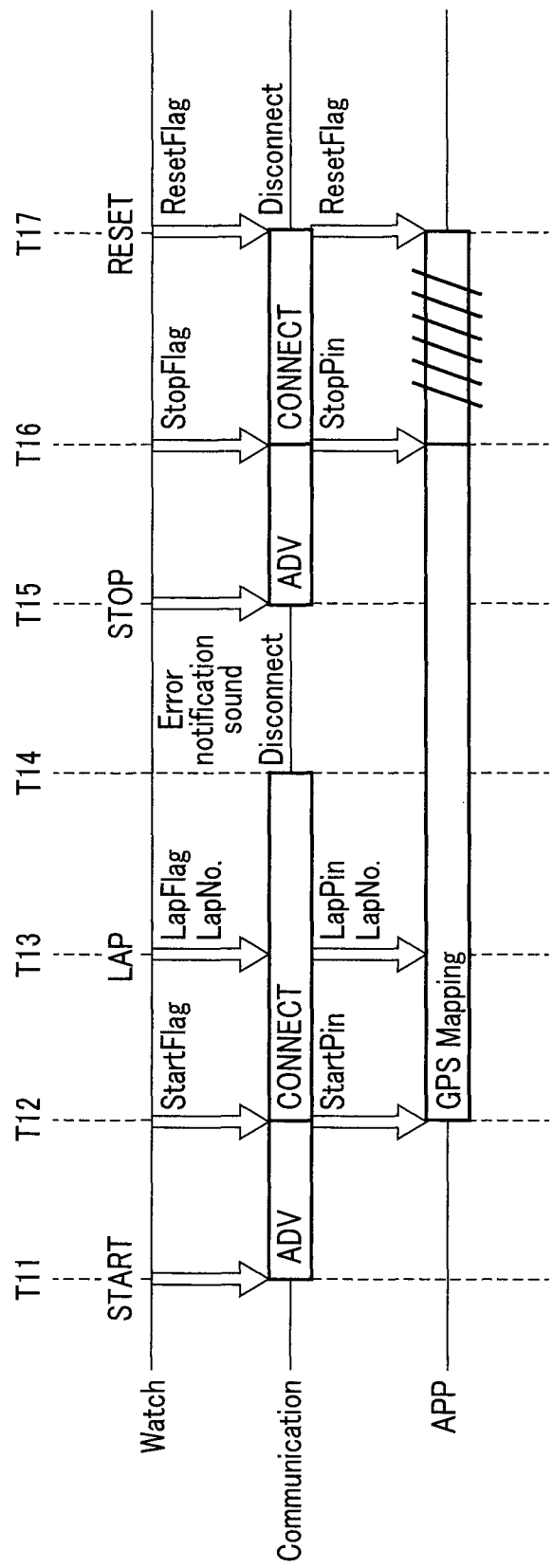
FIG. 7 is a timing chart for illustrating an example of operations of the system of the embodiment.

An example shown in FIG. 7 is described. It is assumed that at time T11, the start button 142 is pressed. At this time, the process of Step S104 in the watch 100 starts measurement, and starts recording. Furthermore, the watch 100 performs the connection process of Step S105, and starts advertising according to the process of Step S141.

It is assumed that at time T12, connection is established. At this time, according to the process of Step S107, the watch 100 transmits the operation information that the start button 142 has been pressed, to the smartphone 200. In the process of Step S204, the smartphone 200 starts position measurement using the satellite positioning system, and starts mapping. The smartphone 200 performs association with start, according to the process of Step S205.

It is assumed that at time T13, the reset button 141 is pressed, and the lap measurement input is performed. According to the process of Step S113, the watch 100 determines the lap time, displays the lap time on the LCD 130, and records the lap time in the memory 114. According to the process of Step S117, the watch 100 transmits the fact that the lap operation has been performed, and the fact that the lap is the first lap, to the smartphone 200. The smartphone 200 having received the information associates the number of laps to thus perform association pertaining to the lap according to the process of Step S210.

It is assumed that at time T14, the connection between the watch 100 and the smartphone 200 is disconnected by electromagnetic interference, timeout or the like, for example. At this time, in Step S112, the watch 100 outputs a sound for notifying the disconnection. Even in the case of disconnection, the smartphone 200 continues recording the current position. By continuing recording the current position, the smartphone 200 can perform processes according to inputs of subsequent operations to the watch 100.

It is assumed that at time T15, the start button 142 is pressed, and the stop input is performed. At this time, according to the process of Step S113, the watch 100 determines the measured time, displays the time on the LCD 130, and records the time in the memory 114. The watch 100 performs the connection process of Step S115, and starts advertising according to the process of Step S141. By starting advertising in response to the operation, establishment of communication during absence of operation is suppressed. As a result, the power consumption is reduced.

It is assumed that at time T16, connection is established. At this time, according to the process of Step S117, the watch 100 transmits, to the smartphone 200, information that the stop command has been input. The smartphone 200 having received the information performs association pertaining to the stop according to the process of Step S210.

It is assumed that at time T17, the reset button 141 is pressed, and the reset input is performed. At this time, according to the process of Step S113, the watch 100 resets the measured time and the display on the LCD 130. According to the process of Step S117, the watch 100 transmits, to the smartphone 200, information that the reset command has been input. The watch 100 transmits the accumulated information required in Step S119, to the smartphone 200. In Step S120, the watch 100 transmits the disconnection request to the smartphone 200. The smartphone 200 having received the information records the information about resetting according to the process of Step S210. The smartphone 200 processes information about the accumulated information according to the process of Step S212. The smartphone 200 disconnects the connection to the watch 100 according to the process of Step S213. As a result, as shown in FIG. 7, the connection is disconnected. The smartphone 200 finishes obtaining the current position information according to the process of Step S214, and removes the position information at the stop at time T16 and thereafter as unnecessary information.

As with this example, when the connection between the watch 100 and the smartphone 200 is disconnected by any reason, a procedure for reconnection is performed at timing on which the next operation is input into the watch 100. Also by such a procedure, the power consumption is reduced.

An example shown in FIG. 8 is described. Behaviors of the watch 100 and the smartphone 200 from time T21 to time T24 are analogous to those in the case described with reference to FIG. 7. It is assumed that at time T24, the connection between the watch 100 and the smartphone 200 is disconnected.

It is assumed that at time T25, the start button 142 is pressed, and the stop input is performed. At this time, according to the process of Step S113, the watch 100 determines the measured time, displays the time on the LCD 130, and records the time in the memory 114. The watch 100 performs the connection process of Step S115, and starts advertising according to the process of Step S141.

It is assumed that at time T26, timeout arrives without establishment of connection. At this time, the watch 100 outputs a sound indicating that a connection can't be established, according to the process of Step S148.

It is assumed that at time T27, the reset button 141 is pressed, and the reset input is performed. At this time, according to the process of Step S113, the watch 100 resets the measurement time and the display on the LCD 130. The watch 100 performs the connection process of Step S115, and starts advertising according to the process of Step S141.

It is assumed that at time T28, timeout arrives without establishment of connection. At this time, the watch 100 outputs a sound indicating that a connection can't be established, according to the process of Step S148. As described above, if connection cannot be established during the operation of the watch 100, information cannot be exchanged between the watch 100 and the smartphone 200. In this case, the timing at which the current position obtaining is stopped cannot be transmitted from the watch 100 to the smartphone 200. In this embodiment, the smartphone 200 is configured to allow the user to input a command for stopping obtaining the current position.

If the command for stopping obtaining the current position is input into the smartphone 200 at time T29, and based on the determination of Step S218, the smartphone 200 finishes the obtaining the current position according to the process of Step S214. At this time, the smartphone 200 cannot obtain the information about the operation to the watch 100. However, at an opportunity of the next connection to the watch 100, the smartphone 200 may obtain the information about the activity, and perform various operations and organize the information based on the information about the activity.

Figure 9:
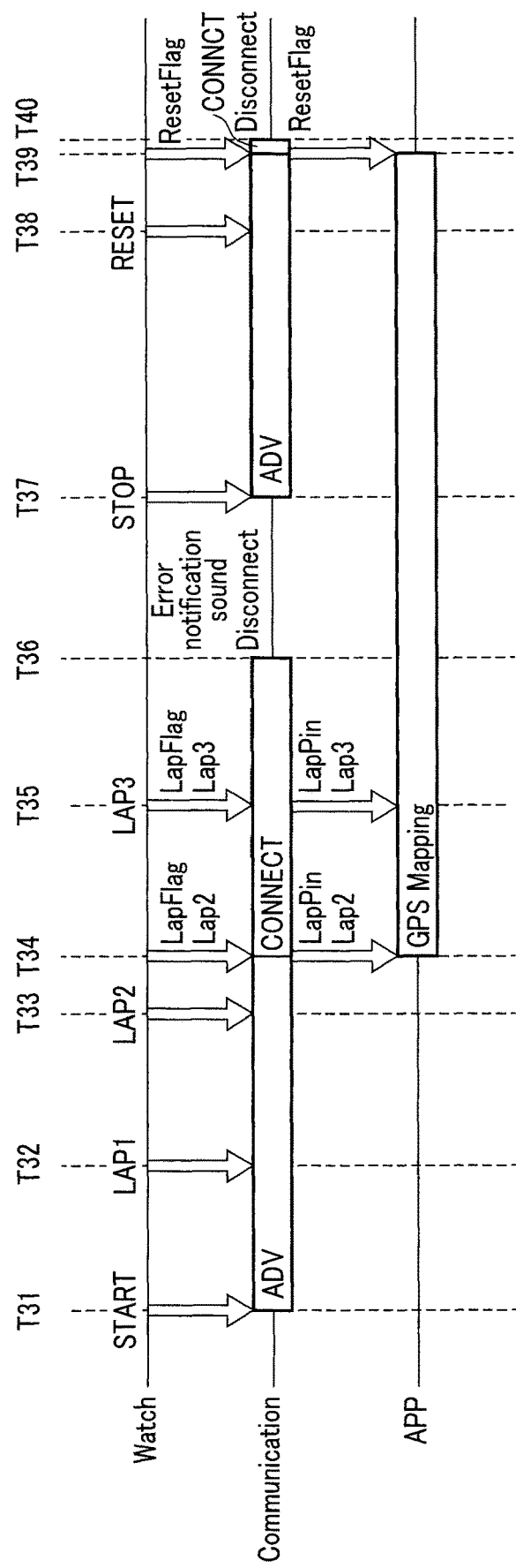
FIG. 9 is a timing chart for illustrating an example of operations of the system of the embodiment.

An example shown in FIG. 9 is described. It is assumed that at time T31, the start button 142 is pressed. At this time, the process of Step S104 in the watch 100 starts measurement, and starts recording. Furthermore, the watch 100 performs the connection process of Step S105, and starts advertising according to the process of Step S141. However, connection between the watch 100 and the smartphone 200 is not established.

It is assumed that at time T32 during advertising, the reset button 141 is pressed, and the lap measurement input is performed. According to the process of Step S147, the watch 100 determines the lap time, displays the lap time on the LCD 130, and records the lap time in the memory 114. The watch 100 continues advertising. However, connection between the watch 100 and the smartphone 200 is not established.

It is assumed that at time T33 during advertising, the reset button 141 is pressed, and the lap measurement input is performed. According to the process of Step S147, the watch 100 determines the lap time, displays the lap time on the LCD 130, and records the lap time in the memory 114. The watch 100 continues advertising.

It is assumed that at time T34, connection is established. At this time, in the process of Step S204, the smartphone 200 starts position measurement using the satellite positioning system, and starts mapping. At this time, according to the process of Step S107, the watch 100 transmits the fact that the lap operation has been performed, and the fact that the lap is the second lap, to the smartphone 200. The smartphone 200 having received the information associates the number of laps to thus perform association pertaining to the lap according to the process of Step S210.

When the start operation and the first lap operation are performed to the watch 100, the watch 100 and the smartphone 200 are not connected to each other. Accordingly, in a case where the start operation is performed and where the first lap operation is performed, the smartphone 200 does not obtain the position information. Accordingly, even if the smartphone 200 obtains any of the information about the start operation and the first lap operation from the watch 100, the smartphone 200 cannot utilize the information. The watch 100 then transmits only the last lap information that is the second lap information to the smartphone 200.

With use of information on the time period from the start to the first lap operation and on the time period from the first lap operation to the second lap operation, the smartphone 200 can obtain the following information. The smartphone 200 can obtain the entire activity time period for these activities. The smartphone 200 can estimate the travel distance from the start to the second lap, based on the travel pace after the second lap. As a result, the smartphone 200 can estimate the entire travel distance for these activities. The smartphone 200 can estimate the average of paces over the entire activities, from the entire travel distance. Accordingly, it is preferred that the information on the time period from the start to the first lap operation and on the time period from the first lap operation to the second lap operation be transmitted, as accumulated information, from the watch 100 to the smartphone 200.

It is assumed that at time T35, the reset button 141 is pressed, and the lap measurement input is performed. According to the process of Step S113, the watch 100 determines the lap time, displays the lap time on the LCD 130, and records the lap time in the memory 114. According to the process of Step S117, the watch 100 transmits the fact that the lap operation has been performed, and the fact that the lap is the third lap, to the smartphone 200. The smartphone 200 having received the information associates the number of laps to thus perform association pertaining to the lap according to the process of Step S210.

It is assumed that at time T36, the connection between the watch 100 and the smartphone 200 is disconnected by electromagnetic interference or timeout, for example. At this time, in Step S112, the watch 100 outputs a sound for notifying the disconnection. Even in the case of disconnection, the smartphone 200 continues recording the current position.

It is assumed that at time T37, the start button 142 is pressed, and the stop input is performed. At this time, according to the process of Step S113, the watch 100 determines the measurement time, displays the time on the LCD 130, and records the time in the memory 114. The watch 100 performs the connection process of Step S115, and starts advertising according to the process of Step S141. However, connection between the watch 100 and the smartphone 200 is not established.

It is assumed that at time T38 during advertising, the reset button 141 is pressed, and the reset input is performed. At this time, according to the process of Step S113, the watch 100 resets the measurement time and the display on the LCD 130. The watch 100 continues advertising.

It is assumed that at time T39, connection is established. At this time, according to the process of Step S117, the watch 100 transmits, to the smartphone 200, information that the reset command has been input. The watch 100 transmits the accumulated information required in Step S119, to the smartphone 200. In Step S120, the watch 100 transmits the disconnection request to the smartphone 200. The smartphone 200 having received the information records the information about resetting according to the process of Step S210. The smartphone 200 processes information about the accumulated information according to the process of Step S212. At time T40, the smartphone 200 disconnects the connection to the watch 100 according to the process of Step S213. The smartphone 200 finishes obtaining the current position information according to the process of Step S214.

In this case, the smartphone 200 has not been obtain the information about the stop operation from the watch 100 because connection has not been established. Accordingly, association pertaining to stop is not performed. Accordingly, the smartphone 200 may hold the information about the history of current positions until resetting, without removing the information. Based on the information that is included in the accumulated information and is on the time when the stop operation is performed or on the elapsed time, the smartphone 200 may identify the position at which the stop operation has been performed, and may perform association. In this case, the smartphone 200 may remove the position information after the stop, as unnecessary information.

As with this example, if a plurality of operations are performed to the watch 100 while no communication can be established between the watch 100 and the smartphone 200, the watch 100 transmits information on the immediately previously performed operation to the smartphone 200. Based on the received information, the smartphone 200 performs association pertaining to the immediately previously performed operation. The watch 100 may transmit, to the smartphone 200, the accumulated information including information that cannot have been transmitted because connection has not been established. Based on the obtained accumulated information, the smartphone 200 may reproduce and estimate the information having not been obtained in real time, as much as possible.

In the above example, for example, in a case where no connection can be established and in a case of disconnection, such facts are notified to the user using a sound. However, such information notification is not limited to a sound. For example, the notification may be through vibrations, display or the like, or its combination with a sound.

Figure 10:
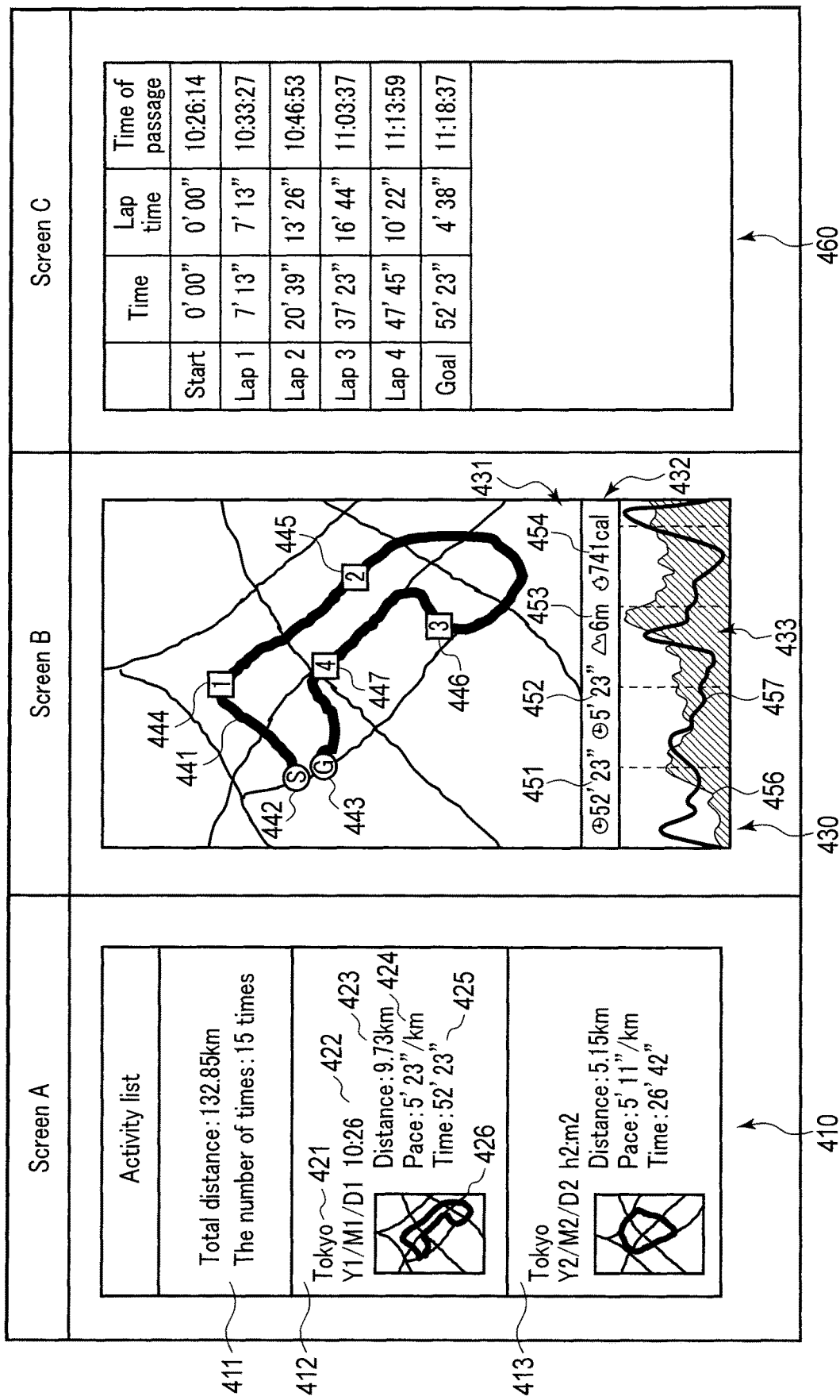
FIG. 10 shows screen examples indicating a history of activities displayed on the smartphone of the embodiment.

An example of a method of presenting, to the user, information obtained by the system 10 in this embodiment is described with reference to FIG. 10. FIG. 10 shows examples of screens displayed on the LCD 230 of the smartphone 200.

When the user wishes to browse a previous record of activities, the smartphone 200 first presents a list screen 410 of a history of activities, as on a screen A. In this example, various total values of activities satisfying a condition set by the user, such as information on past one month, and the entire recorded information, for example, are displayed in a total field 411. For example, the total travel distance, the number of activities and the like are displayed. Other information, such as a total time period for activities, and an average pace over all the activities, may be displayed.

Below the total field 411, summaries of history of activities are displayed. FIG. 10 shows two summaries, i.e., a first summary 412 and a second summary 413. However, by scrolling the screen downward, other summaries are also displayed.

Each summary field includes a place name display 421 indicating a city name where an activity is performed, and a date-and-time display 422 indicating the date and time when the activity is performed. The summary field further includes a distance display 423 indicating the distance of travel during the activity, a pace display 424 indicating the pace, which is the spent time period per unit distance, and a time display 425 indicating the total of time periods for activities. The summary field further includes a map display 426 including a reduced-size map representing the history of travel during activities.

The user can select an activity about which the user intends to view more detailed information, from these summary fields. When the user selects any activity, a map screen 430 as displayed on screen B is displayed, for example. The map screen 430 can include a map area 431, a numeric value area 432, and a graph area 433.

A trajectory display view where the trajectory of the current position information obtained by the smartphone 200 during activities is displayed as a line 441 on a map, is displayed in the map area 431. The smartphone 200 can obtain map information from a predetermined server. The smartphone 200 draws the trajectory of the current position information varying with the lapse of time, on the obtained map. At this time, based on the associated information, the smartphone 200 clearly displays, on the map, for example, the position where the start operation has been performed, as a start display 442, and displays the position where the stop operation has been performed, as a goal display 443. Likewise, a first lap display 444, a second lap display 445, a third lap display 446 and a fourth lap display 447, which indicate the respective positions where the first to fourth lap operations have been performed, are further displayed also on the map, for example. The user views the diagram displayed in the map area 431, thereby allowing the user to grasp the route along which the user has run, and the positions at which lap measurement has been performed.

The numeric value area 432 includes numeric values indicating various types of information, such as a display 451 indicating the total measurement time, a display 452 indicating the pace, a display 453 indicating the maximum height difference of positions during measurement, and a display 454 indicating the calorie estimated to be consumed, for example. The user views the numeric values displayed in the numeric value area 432, thereby allowing the user to grasp the state of activities during measurement by the numerical value.

A graph area 433 includes a graph that indicates the elapsed time on the abscissa axis, and indicates the values of various types of information on the ordinate axis, for example. The graph area 433 can include, for example, a graph 456 indicating the altitude at the current position, and a graph 457 indicating the pace. The user views the graph area 433, thereby allowing the user to identify visually the variation in various values on the graph with the lapse of time during activities.

When a swipe operation is performed in a predetermined direction on the map screen 430 or when a predetermined icon is selected, a time screen 460 as indicated on a screen C is displayed. Information about the elapsed time measured and recorded in the watch 100 is displayed on the time screen. The smartphone obtains the information from the watch 100 through communication. As shown in FIG. 10, elapsed times at the start, the laps and the goal, and the lap times and the times thereat are displayed on the time screen 460 in a table format. The user views the time screen 460, thereby allowing the user to view the information about the elapsed times measured in the watch 100.

As for the start position, for example, a difference of a time period required to establish communication between the watch 100 and the smartphone 200 occurs between positions at which the user has operated the watch 100, that is, the position at which the time has been measured by the operation, and the position with which association has been performed by the smartphone 200. Accordingly, a difference can occur between the information displayed on the map screen 430, and the information displayed on the time screen 460. In consideration of the difference, the map screen 430 and the time screen 460 may be displayed as different screens.

According to this embodiment, operation in cooperation between the watch 100 into which the operation by the user is input and which measures the elapsed time, and the smartphone 200 that obtains the current position through the satellite positioning system, can present, to the user, valuable information as shown in FIG. 10.

Typically, many users carry smartphones during running. In this embodiment, a position obtaining role that uses the satellite positioning system and consumes much power is played by the smartphone 200, thereby allowing the power consumption by the watch 100 to be reduced.

It is easy for the user to operate the watch 100 worn on a wrist in an exposed state even during running, for example. In this embodiment, the operations, such as of the start, stop and lap, are performed using the watch 100. Accordingly, the operability of the system 10 is favorable.

In the embodiment described above, the start of the stopwatch, and the start of connection operation between the watch 100 and the smartphone 200 are associated with each other. Alternatively, the watch 100 may be configured to accept an operation for starting the connection operation with the smartphone 200 before the start of the stopwatch. However, association between the start of the stopwatch and the start of the connection operation allows the user to use this system with a simple operation analogous to that of a typical stopwatch without awareness of the communication situations.

The start operation starts communication, and the reset operation finishes the communication. Consequently, the watch 100 and the smartphone 200 communicate with each other only during measurement by the watch 100. The power consumption of the watch 100 can be reduced accordingly.

In the smartphone 200, the start operation starts obtaining the current position using the positioning system, and the reset operation finishes the current position obtaining. The power consumption of the smartphone 200 by positioning can be reduced accordingly.

In the embodiments described above, the watch having the stopwatch function is described as an example of the wrist information device fixed to a wrist of a user. However, the embodiments are not limited thereto. The wrist information device may be a device that only accepts a command of an operation by the user but does not have a function as a stopwatch. As described in the above embodiments, the wrist information device has the watch having the stopwatch function, thereby allowing the user to identify the elapsed time during activities. The wrist information device is not limited to what has the timepiece function and stopwatch function. Alternatively, this device may be an information terminal having various functions of transmitting and receiving email, such as what is called a smartwatch or the like.

This technique is not limited to application to the wrist information device worn on the wrist, and is applicable also to terminals worn on other parts of the body of the user, such as an eyeglasses-type device. Furthermore, this technique is not limited to application to position detection using the satellite positioning system, and is applicable also to cases of using position detection through other methods.

The present invention is not limited to the embodiments described above. In an implementation stage, the present invention can be variously modified in a range without departing from the gist thereof. Each embodiment can be appropriately combined and implemented. In this case, combined advantageous effects can be achieved.

The invention claimed is:

1. An information terminal configured to be used with a wrist information device comprising an operation receiver and having a clock function, the information terminal comprising:
   a position measurement module configured to obtain position information using a satellite positioning system;
   a communication circuit configured to be capable of communication with the wrist information device;
   a memory; and
   a processor,
   wherein the processor is configured to:
   obtain information about an operation of the clock function input into the wrist information device, from the wrist information device via the communication circuit, during establishment of connection of the communication,
   obtain the position information obtained using the satellite positioning system, from the position measurement module,
   store, in the memory, the position information and the information about the operation of the clock function in association with each other,
   obtain, via the communication circuit, the information about an elapsed time measured at the operation of the clock function, the information having been transmitted from the wrist information device, and
   store, in the memory, the position information, the information about the operation of the clock function and information about the elapsed time, in association with each other.

2. The information terminal according to claim 1,
wherein the information about the operation of the clock function includes information about an operation of start of measuring an elapsed time in the clock function, and
the processor is further configured to:
   obtain a signal of a request for the connection of the communication, via a communication circuit, the signal having been transmitted from the wrist information device upon input of the operation of start,
   cause the communication circuit to establish connection between the wrist information device and the information terminal, based on the signal of the request for the connection, and
   obtain, via the communication circuit, the information about the operation of start transmitted from the wrist information device.

3. The information terminal according to claim 2,
wherein the processor causes the communication circuit to establish the connection, and starts obtaining the position information from the position measurement module.

4. The information terminal according to claim 2,
wherein the information about the operation of the clock function includes information about an operation of reset of measuring an elapsed time in the clock function,
the processor is further configured to cause the communication circuit to disconnect the connection, when the processor receives, via the communication circuit, the information about the operation of reset transmitted from the wrist information device.

5. The information terminal according claim 2,
wherein the processor is further configured to:
   obtain, via the communication circuit, the information about an elapsed time measured at the operation of the clock function, the information having been transmitted from the wrist information device, and
   store, in the memory, the position information, the information about the operation of the clock function and the elapsed time, in association with each other.

6. The information terminal according to claim 2,
wherein the information about the operation of the clock function includes information about operations of stop and reset of measuring an elapsed time in the clock function, and
the processor is further configured to remove the position information obtained from the position measurement module, after obtaining the information about the operation of stop and before obtaining the information about the operation of reset, via the communication circuit.

7. The information terminal according to claim 2,
wherein the processor is further configured to:
obtain, via the communication circuit, information including a history about the operation of the clock function, the information having been recorded and transmitted by the wrist information device,
create information on an activity history, using the information including the history, and
store the information on the activity history, in the memory.

8. The information terminal according to claim 2,
wherein the processor is further configured to:
cause the communication circuit to disconnect the connection, when the information about the operation of the clock function transmitted from the wrist information device is not obtained for a predetermined time period, and
continue obtaining the position information from the position measurement module, even after disconnecting the connection.

9. The information terminal according to claim 2, wherein the connection is performed by Bluetooth Low Energy.

10. The information terminal according to claim 1,
wherein the information about the operation of the clock function includes information about an operation of reset of measuring an elapsed time in the clock function,
the processor is further configured to cause the communication circuit to disconnect the connection, when the processor receives, via the communication circuit, the information about the operation of reset transmitted from the wrist information device.

11. The information terminal according to claim 10,
wherein the processor causes the communication circuit to disconnect the connection, and finishes obtaining the position information from the position measurement module.

12. The information terminal according to claim 1,
wherein the information about the operation of the clock function includes information about operations of stop and reset of measuring an elapsed time in the clock function, and
the processor is further configured to remove the position information obtained from the position measurement module, after obtaining the information about the operation of stop and before obtaining the information about the operation of reset, via the communication circuit.

13. The information terminal according to claim 1,
wherein the processor is further configured to:
obtain, via the communication circuit, information including a history about the operation of the clock function, the information having been recorded and transmitted by the wrist information device,
create information on an activity history, using the information including the history, and
store the information on the activity history, in the memory.

14. The information terminal according to claim 13,
wherein the information including the history further includes information about the operation of the clock function while the connection is not established, and
based on the information including the history, the processor creates the information on the activity history including the information about the operation of the clock function while the connection is not established.

15. The information terminal according to claim 1,
wherein the processor is further configured to:
cause the communication circuit to disconnect the connection, when the information about the operation of the clock function transmitted from the wrist information device is not obtained for a predetermined time period, and
continue obtaining the position information from the position measurement module, even after disconnecting the connection.

16. The information terminal according to claim 1, wherein the connection is performed by Bluetooth Low Energy.

17. A wrist information device configured to be used with an information terminal configured to be capable of obtaining position information using a satellite positioning system, the wrist information device comprising:
a communication circuit configured to be capable of communicating with the information terminal;
an operation receiver; and
a processor, wherein the processor is configured to:
execute a clock function,
transmit information about an operation of the clock function, to the information terminal via the communication circuit, the information having been input into the operation receiver to be recorded in association with the position information obtained using the satellite positioning system, in the information terminal, during establishment of connection of the communication with the information terminal,
transmit, via the communication circuit, a signal of a request for the connection of the communication, when the operation of the clock function is input into the operation receiver while connection of the communication is not established,
transmit the information about the operation of the clock function to the information terminal via the communication circuit, when the connection between the wrist information device and the information terminal is established, based on the signal of the request for the connection, the connection being to be established by the information terminal, and
transmit the information about the operation of the clock function received by the operation receiver immediately after establishment of the connection, to the information terminal via the communication circuit, when a next operation of the clock function is input into the operation receiver after output of the signal of the request for the connection and before the establishment of the connection.

18. A system comprising:
a wrist information device comprising an operation receiver and having a clock function; and
an information terminal configured to be capable of obtaining position information using a satellite positioning system, and be capable of communication with the wrist information device,
wherein the wrist information device transmits the information about an operation of the clock function, during establishment of connection of the communication, the information having been input into the wrist information device, and
the information terminal
stores the position information obtained using the satellite positioning system, and the information about the operation of the clock function, in association with each other, obtains, via the communication circuit, the information about an elapsed time measured at the operation of the clock function, the information having been transmitted from the wrist information device, and stores, in a memory, the position information, the information about the operation of the clock function and information about the elapsed time, in association with each other.

19. An information terminal configured to be used with a wrist information device comprising an operation receiver and having a clock function, the information terminal comprising:

a position measurement module configured to obtain position information using a satellite positioning system;

a communication circuit configured to be capable of communication with the wrist information device;

a memory; and a processor, wherein the processor is configured to:

obtain information about an operation of the clock function input into the wrist information device, from the wrist information device via the communication circuit, during establishment of connection of the communication, obtain the position information obtained using the satellite positioning system, from the position measurement module, store, in the memory, the position information and the information about the operation of the clock function in association with each other, obtain, via the communication circuit, information including a history about the operation of the clock function, the information having been recorded and transmitted by the wrist information device, create information on an activity history, using the information including the history, and store the information on the activity history, in the memory, wherein the information including the history further includes information about the operation of the clock function while the connection is not established, and based on the information including the history, the processor creates the information on the activity history including the information about the operation of the clock function while the connection is not established.

20. A wrist information device configured to be used with an information terminal configured to be capable of obtaining position information using a satellite positioning system, the wrist information device comprising:

a communication circuit configured to be capable of communicating with the information terminal;

an operation receiver; and a processor, wherein the processor is configured to:

execute a clock function, and transmit information about an operation of the clock function and information about an elapsed time measured at the operation of the clock function, to the information terminal, the information terminal storing, in a memory, the position information, the information about the operation of the clock function and information about the elapsed time, in association with each other.

* * * * *